United States Patent
Farmer et al.

(10) Patent No.: US 9,267,993 B2
(45) Date of Patent: Feb. 23, 2016

(54) BATTERY MANAGEMENT SYSTEM WITH DISTRIBUTED WIRELESS SENSORS

(71) Applicant: Lawrence Livermore National Security, LLC, Livermore, CA (US)

(72) Inventors: Joseph C. Farmer, Tracy, CA (US); Todd M. Bandhauer, Livermore, CA (US)

(73) Assignee: Lawrence Livermore National Security, LLC, Livermore, CA (US)

(*) Notice: Subject to any disclaimer, the term of this patent is extended or adjusted under 35 U.S.C. 154(b) by 475 days.

(21) Appl. No.: 13/772,620

(22) Filed: Feb. 21, 2013

(65) Prior Publication Data

US 2013/0314094 A1 Nov. 28, 2013

Related U.S. Application Data

(60) Provisional application No. 61/650,649, filed on May 23, 2012.

(51) Int. Cl.

| G01N 27/416 | (2006.01) |
|---|---|
| G01R 31/36 | (2006.01) |
| G01N 25/20 | (2006.01) |
| G01N 29/14 | (2006.01) |
| H01M 10/48 | (2006.01) |
| H01G 11/10 | (2013.01) |
| H01G 11/18 | (2013.01) |
| H01M 10/0525 | (2010.01) |

(52) U.S. Cl.
CPC ............ *G01R 31/3606* (2013.01); *G01N 25/20* (2013.01); *G01N 29/14* (2013.01); *H01G 11/10* (2013.01); *H01G 11/18* (2013.01); *H01M 10/482* (2013.01); *H01M 10/486* (2013.01); *G01R 31/3689* (2013.01); *H01M 10/0525* (2013.01); *Y02E 60/13* (2013.01); *Y02T 10/7011* (2013.01); *Y02T 10/7022* (2013.01)

(58) Field of Classification Search
USPC ........................................................ 324/430
See application file for complete search history.

(56) References Cited

U.S. PATENT DOCUMENTS

| 6,184,656 | B1* | 2/2001 | Karunasiri et al. ........... 320/119 |
| 8,084,154 | B2 | 12/2011 | Scheucher |
| 2009/0140870 | A1* | 6/2009 | Densham ................. 340/636.15 |
| 2010/0279159 | A1 | 11/2010 | Meintschel et al. |
| 2012/0090402 | A1* | 4/2012 | Hojo ............................... 73/788 |
| 2012/0182021 | A1 | 7/2012 | McCoy et al. |

FOREIGN PATENT DOCUMENTS

WO 2012097965 A2 7/2012

* cited by examiner

*Primary Examiner* — Robert Grant
(74) *Attorney, Agent, or Firm* — Eddie E. Scott

(57) ABSTRACT

A system for monitoring parameters of an energy storage system having a multiplicity of individual energy storage cells. A radio frequency identification and sensor unit is connected to each of the individual energy storage cells. The radio frequency identification and sensor unit operates to sense the parameter of each individual energy storage cell and provides radio frequency transmission of the parameters of each individual energy storage cell. A management system monitors the radio frequency transmissions from the radio frequency identification and sensor units for monitoring the parameters of the energy storage system.

3 Claims, 13 Drawing Sheets

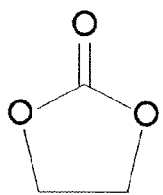

EC = ethylene carbonate
1,3 dioxolan-2-one-1
$3/2\, Li_xCoO_2 + C_3H_4O_3 \rightarrow 3CO_2 + 2H_2 + 3/2\, Li_xCo$
$5/2\, Li_xCoO_2 + C_3H_4O_3 \rightarrow 3CO_2 + 2H_2O + 5/2\, Li_xCo$

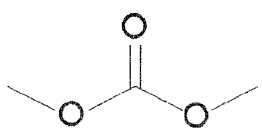

DMC = dimethyl carbonate
carbonic acid dimethyl ester
$3/2\, Li_xCoO_2 + C_3H_6O_3 \rightarrow 3CO_2 + 3H_2 + 3/2\, Li_xCo$
$6/2\, Li_xCoO_2 + C_3H_6O_3 \rightarrow 3CO_2 + 3H_2O + 6/2\, Li_xCo$

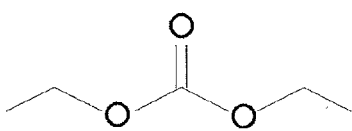

DEC = diethyl carbonate
carbonic acid diethyl ester
$7/2\, Li_xCoO_2 + C_5H_{10}O_3 \rightarrow 5CO_2 + 5H_2 + 7/2\, Li_xCo$
$12/2\, Li_xCoO_2 + C_5H_{10}O_3 \rightarrow 5CO_2 + 5H_2O + 12/2\, Li_xCo$

FIG. 16

BATTERY MANAGEMENT SYSTEM WITH DISTRIBUTED WIRELESS SENSORS

CROSS-REFERENCE TO RELATED APPLICATIONS

This application claims benefit under 35 U.S.C. §119(e) of U.S. Provisional Patent Application No. 61/650,649 filed May 23, 2012 entitled "Lithium Ion Battery Management System with Distributed Wireless & Fiber Optic Sensors, and Embedded Fire Suppression System," the disclosure of which is hereby incorporated herein by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to energy storage management systems including advanced battery management systems, systems for managing other energy storage systems, and systems for managing lithium ion and other batteries.

2. State of Technology

Lithium-ion batteries are proven technology, and are leading candidates for terrestrial electric vehicles, back-up power in airplanes and many other uses. Virtually all modern cellular telephones and portable computers use lithium-ion batteries for energy storage. Other important applications of this technology include emerging electric vehicles, such as the Tesla sports car, various autonomous underwater vehicles (AUVs), manned underwater vehicles (UUVs), the Mars Rover, and large laser systems.

This technology has also enjoyed limited but successful use in autonomous underwater vehicles used for oceanographic research. Unfortunately, lithium ion batteries have been plagued by a history of significant safety incidents, with some causing serious human injury and property damage (loss of commercial cargo plane, for example). The lithium-acid battery may prove to be relatively expensive, has safety issues that must be dealt with, but has exceptional performance characteristics, that make it a leading candidate for consideration. Designs would have to emphasize safety, thermal management during charge and discharge, and enhanced battery management systems.

Codes for BMS control algorithms have unique attributes, in that they enable the simultaneous solution of those equations that account for the flow of fluid and heat, chemical reactions, current flow and mechanical stress. However, the equations that describe electrode kinetics and ionic transport have not yet been integrated into the code.

The modern lithium-ion battery has: an anode that consists of a graphite-based active material (Li—C6) with carbon filler and PVDF binder coated onto a copper foil current collector; a cathode that consists of a transition metal oxide or iron phosphate (Li—NiO2, Li—CoO2, Li—MnO2, or Li—FePO4) active material with a PVDF binder coated onto an aluminum foil current collector; a microporous porous polyethylene separator, and an electrolyte consisting of a mixed organic carbonate solvent (EC:DMC:DEC) and LiPF6 salt. The liquid cylindrical or prismatic cells are contained in a hermetically sealed metal can, while polymer-gel cells are contained in a soft aluminum-polyethylene laminate package, with thermally laminated seams. In the case of the polymer-gel cell, the polyethylene separator is usually coated on both sides with porous PVDF layers.

This battery can operate from −40 to +60 degrees Centigrade. The open-circuit voltage is 4.1 V, with operation between 4.0 and 3.0V (possibly as low as 2.8 V). The specific power, power density, specific energy and energy density are 1100-74 W/kg, 2270-147 W/L, 75-182 Wh/kg, and 139-359 Wh/L, respectively. The cycle life of the best state-of-the-art lithium-ion batteries can be as great as 1500 cycles (to 80% of the original capacity). However, poorly constructed cells can have much shorter lives (300 cycles representing poorer cells). Based upon published data, the cost of energy storage is believed to be approximately $300 per kilowatt-hour (though some quote $1000 per kilowatt-hour).

One key advantage of such flow batteries is the ability to scale the batteries capacity linearly with the size of the reservoirs used for storing the anolyte and catholyte. Other advantages include thermal management, efficiency, and the relative ease of construction. The ZnBr battery was patented over 100 years ago, but has never enjoyed widespread commercialization. Technical problems have included the formation of zincdendrites during repeated charging and discharging, which can lead to internal shorts within the cell, and the relatively high solubility of Br in the aqueous electrolyte required by the Zn electrode.

The modern lithium ion battery was developed to overcome safety problems encountered with early rechargeable batteries with metallic lithium anodes. Metallic lithium can react with a wide variety of polymeric materials involved in cell construction, including but not limited to fluorinated polymers such as Teflon. In contrast, the lithium ion battery involves two intercalation electrodes which serve as "nanoscale parking garages" for reduced metallic lithium atoms, thereby avoiding the presence of free metallic lithium in the cell. The use of these two intercalation electrodes, with lithium being shuttled from one parking garage to the other is known as the "rocking chair mechanism" which the intercalation cathode is usually a transition metal oxide or iron phosphate, and the intercalation anode is usually a natural or synthetic graphite. In some cases, lithium alloys such as Li—Sn or Li—Si are used in lieu of graphite.

One problem encountered with advanced battery systems, including lithium ion batteries which rely on the formation of lithium-intercalation compounds at both electrodes, is the plating of dangerous metallic lithium on either the anode active material (graphite) or cathode active material (transition metal oxide or iron phosphate) during repeated cycling. This problem can be exacerbated by attempts to quickly recharge the battery, which will be a temptation in automotive applications. Who wants to wait an hour or two at the filling station to refuel their car? If there is a failure to maintain good contact between adjacent pressure with uniform stack.

The avoidance of lithium plating requires precise understanding of the primary and secondary current distributions inside individual cells, not only at the electrode scale, but also on the length scale of individual micron-sized particles of active material, and on the scale of interatomic spacing in the intercalation compounds that are formed. In addition to modeling the other complexities of the batteries and battery packs (series-parallel strings of individual cells), which include thermal transport and mechanical stresses, it is necessary to make precise predictions of the current and potential distribution between the anodes and cathodes, as well around the individual particles of active material on both electrodes. The physics that must be well understood before predictable and reliable battery packs can be designed include: battery chemistry of nominal charge/discharge; abnormal ageing at a defect (local chemistry, heat, voltage, stress); electric fields and current flow within the cell; heat generation and cell cooling, thermal run-away; convection fluid flow within the electrolyte; external coolant flow; stress and material failure due to volumetric changes during charge/discharge cycle; chemical deflagration of run-away battery; dynamic structural failure of run-away battery cell and battery system; in principle, modern computational modeling could be applied to the design of high performance batteries and battery packs, to help ensure that robust, thermally-stable systems have been built.

Safety is the leading show-stopper for large Li-ion cells, and the battery packs built from those cells. Despite decades of conventional safety testing serious problems remain. Lithium-ion explosions and fires occur frequently in both products and manufacturing plants. In regard to electric vehicle applications, statistics indicates that 1 in every ~30,000 electric vehicles with a lithium ion battery pack will burn and/or explode. Given that an electric vehicle with a 100-mile range is capable of releasing a quantity of energy equivalent to ~500 sticks of dynamite, this is alarming.

As a lithium ion battery begins to undergo heating, which can be caused by ohmic heating, internal shorting, or the application of heat from outside the cell, a sequence of chemical reactions occur within the Li-ion system, ultimately leading to thermal runaway. During such catastrophic events, numerous chemical reactions begin occurring sequentially. While the inside of the Li-ion cell is oxygen-free, enough oxygen can be liberated from the decomposition of the transition metal oxide active material in the cathode during thermal runaway, regardless of the initiating event, to support limited combustion of the organic carbonate solvents in the electrolyte. Localized internal shorts quickly drive such high performance energy storage systems into thermal runaway, with subsequent propagation to other lithium-ion cells in the battery pack, with further propagation to other packs within the system if they exist.

International Patent Application No. WO 2010/025761 for a system for fire protection provides state of technology information including the following information: "The batteries of the backup power thus contain high amount of energy, and a failing battery cell, e.g. by external or internal short circuit or overload, will quickly become very hot. The heat emitted from the failing cell will heat up an adjacent battery cell, which in turn will heat up the next cell and so on, and this of course constitutes a huge fire hazard. As an example, Li-ion battery cells exceeding a critical temperature may result in opening of the cell, known as venting of the cell, with a release of highly inflammable gases that can easily catch fire. If this happens there is a large risk of the whole battery storage system being destroyed." The disclosure of International Patent Application No. WO 2010/025761 is incorporated herein in its entirety for all purposes by this reference.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides monitoring parameters of an energy storage system that includes one or more energy storage packs having a multiplicity of individual energy storage cells. The present invention utilizes radio frequency identification and detection of the individual energy storage cells for identification and detection of the parameters of each individual energy storage cell. A management system monitors the radio frequency identification and detection of the parameters of each individual energy storage cell. The parameters include one or more of the following parameters: cell voltage, cell current, cell impedance, cell temperature, cell internal pressure, stress and strain in the cell, electrolyte leakage, gas evolution and leakage, optical and nuclear particle transmission and scattering, and/or pyrotechnic displays.

In various embodiments, the present invention provides a system for wirelessly monitoring a very large number of spatially-distributed parameters in a high-capacity electrochemical energy storage system, where each parameter is indicative of the energy storage system's "state of health" and "operational safety." The energy storage system includes one or more energy storage packs having a multiplicity of individual energy storage cells.

The present invention utilizes radio frequency identification and detection (RFID) of the sensors used to monitor individual energy storage cells. These wireless sensors and RFID tags are used to identify and detect operational parameters for each individual energy storage cell in a much larger series-parallel array. A management system monitors the radio frequency identification and detection of the parameters of each individual energy storage cell. The parameters include one or more of the following parameters: cell voltage, cell current, cell impedance, cell temperature, cell internal pressure, stress and strain in the cell, electrolyte leakage, gas evolution and leakage, optical and nuclear particle transmission and scattering, and/or pyrotechnic displays.

In one embodiment, the present invention provides an apparatus for monitoring parameters of a lithium ion battery system that includes one or more lithium ion battery packs having a multiplicity of individual lithium ion battery cells. The apparatus includes a radio frequency identification and detection unit connected to each of the individual lithium ion battery cells for identification and detection of the parameters of the lithium ion battery cell and a management system for monitoring the radio frequency identification and detection units for monitoring parameters the energy storage system. The parameters being monitored can include one or more of the following parameters: cell voltage, cell current, cell impedance, cell temperature, cell internal pressure, stress and strain in the cell, electrolyte leakage, gas evolution and leakage, acoustic emissions, optical emissions due to the pyrotechnic displays that usually accompany venting, and other signals indicative of the cells state-of-health and operational safety.

In another embodiment, the present invention provides an apparatus for monitoring parameters of a large capacitor bank energy storage system that includes one or more capacitor banks having a multiplicity of individual capacitor cells. The apparatus includes a radio frequency identification and detection unit connected to each of the individual capacitor cells for identification and detection of the parameters of the capacitor cell and a management system for monitoring the radio frequency identification and detection units for monitoring parameters the capacitor bank energy storage system.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 16 illustrates the combustion of organics supported by disproportionation of cathode materials.

DETAILED DESCRIPTION OF SPECIFIC EMBODIMENTS

Figure 1:
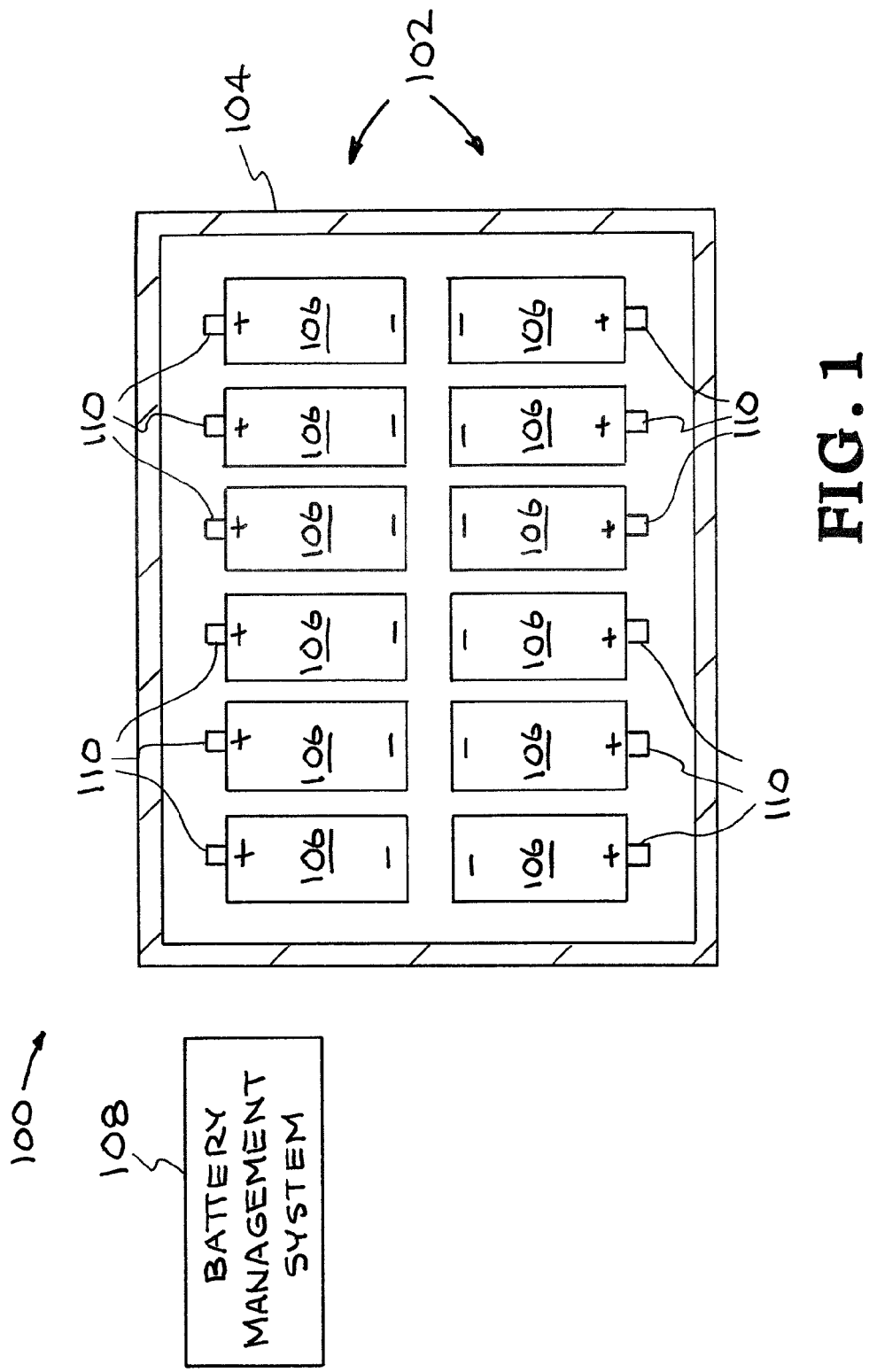
FIG. 1 illustrates a battery management system constructed in accordance with the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

There is a need for an advanced management system for energy storage devices. There is also a need for a battery management system that will provide detailed information about conditions in the individual cells of a battery and that will report and provide documentation of the detailed information about conditions in the individual cells of a battery. For example, lithium ion batteries have been plagued by a history of significant safety incidents, with some causing serious human injury and property damage (loss of commercial cargo plane, for example). The Jan. 17, 2013 article, "*The battery that grounded Boeing*" in CNN Money stated: "U.S. officials grounded Boeing's new 787 Dreamliner because the aircraft's advanced batteries appear to be malfunctioning. But what's the problem? And can it be fixed? To reduce weight on the plane, Boeing relied heavily on lithium ion batteries—the same type found in mobile phones and laptops. While these batteries can produce a lot of power for their weight, they're also prone to problems. It was these same batteries that caught fire in laptops a few years back and, more recently, were suspected culprits in electric car fires." The Jan. 28, 2013 article, "*Problem in Boeing 787 planes still baffles*" in *The Boston Globe* stated: "Although a fire destroyed one of two big batteries on a Boeing 787 parked at Logan International Airport in Boston three weeks ago, a quick examination of the second battery found "no obvious anomalies," the National Transportation Safety Board said Sunday . . . . The batteries use a lithium-ion chemistry, which has been in use for many years in many applications but is new in airplanes. Investigators say the problem could be the batteries or with the associated electronics used to manage them."

Applicant's present invention provides a solution to the lithium ion battery problems by providing a battery management system. Applicant's invention will be further explained, illustrated, and described in the following examples of systems constructed in accordance with the present invention. The examples demonstrate the utility and/or function of the invention and help provide a full describe of the invention. The examples are intended to be illustrative and not limitative of the present invention.

Battery Management System

Referring now to the drawings and in particular to FIG. 1, one embodiment of a battery management system constructed in accordance with the present invention is illustrated. The system is designated generally by the reference numeral 100. The system 100 includes any number of battery modules or battery packs 102 within a battery pack housing 104. Each individual battery module or pack 102 includes any number of individual battery cells 106. The battery module or pack 102 may for example comprise a number of series-connected and/or parallel-connected battery cells 102 housed within the battery pack housing 104.

Each individual battery module or pack 102 includes any number of individual battery cells 106 and a corresponding number of Radio Frequency Identification (RFID) sensors 110. A remote battery management system 108 is operatively connected to the battery module or pack 102, the battery cells 106, and the Radio Frequency Identification (RFID) sensors 110 in the housing 104.

The system 100 provides an advanced battery management system for the battery module or pack 102 and the battery cells 106 using the Radio Frequency Identification (RFID) sensors 110. The system 100 enables detection of various events in the battery module or pack 102 and the battery cells 106. The remote battery management system 108 enables remedial action.

Referring again to FIG. 1, a system is illustrated that in one embodiment can consist of large series-parallel arrays of high performance battery cells. The system 100 enables the early detection of various events in the high capacity battery packs to provide rapid response to prevent and suppress such events before the results become catastrophic. The distributed wireless sensors 110 enable the detection of various parameter including one or more of the following parameters: cell voltage, cell current, cell impedance, cell temperature, cell internal pressure, stress and strain in the cell package, electrolyte leakage, gas evolution and leakage, optical and nuclear particle transmission and scattering, and any pyrotechnic displays internal to the battery pack that may be attributed to the onset of thermal runaway. The sensors 110 may be either active or passive, with communication possible via the RFID components. Once the sensors 110 detect the onset of an event, the signal is used to appropriately manage pack operation (charge and discharge), and remedial action systems will be activated.

The system 100 also leverages specialized computer models and codes as control algorithms in a smart battery management system (BMS) unique attributes, enables simultaneous solution of those equations that account for the flow of fluid and heat, chemical reactions, current flow and mechanical stress. The equations that describe electrode kinetics and ionic transport will be integrated into the code. This modeling enables designers to account for subtle, but very important effects such as damage of local circuitry and other vehicular components by the pyrotechnic venting of hot gases. Effective cooling systems, and engineered "fire breaks" and "internal fire suppression methods" can be included. The system 100 has many uses, for example the system 100 has use in connection with high capacity lithium ion battery packs for electric and hybrid-electric vehicles, naval systems, aerospace systems, grid storage, and uninterruptable power supplies.

Capacitor Management System

Figure 2:
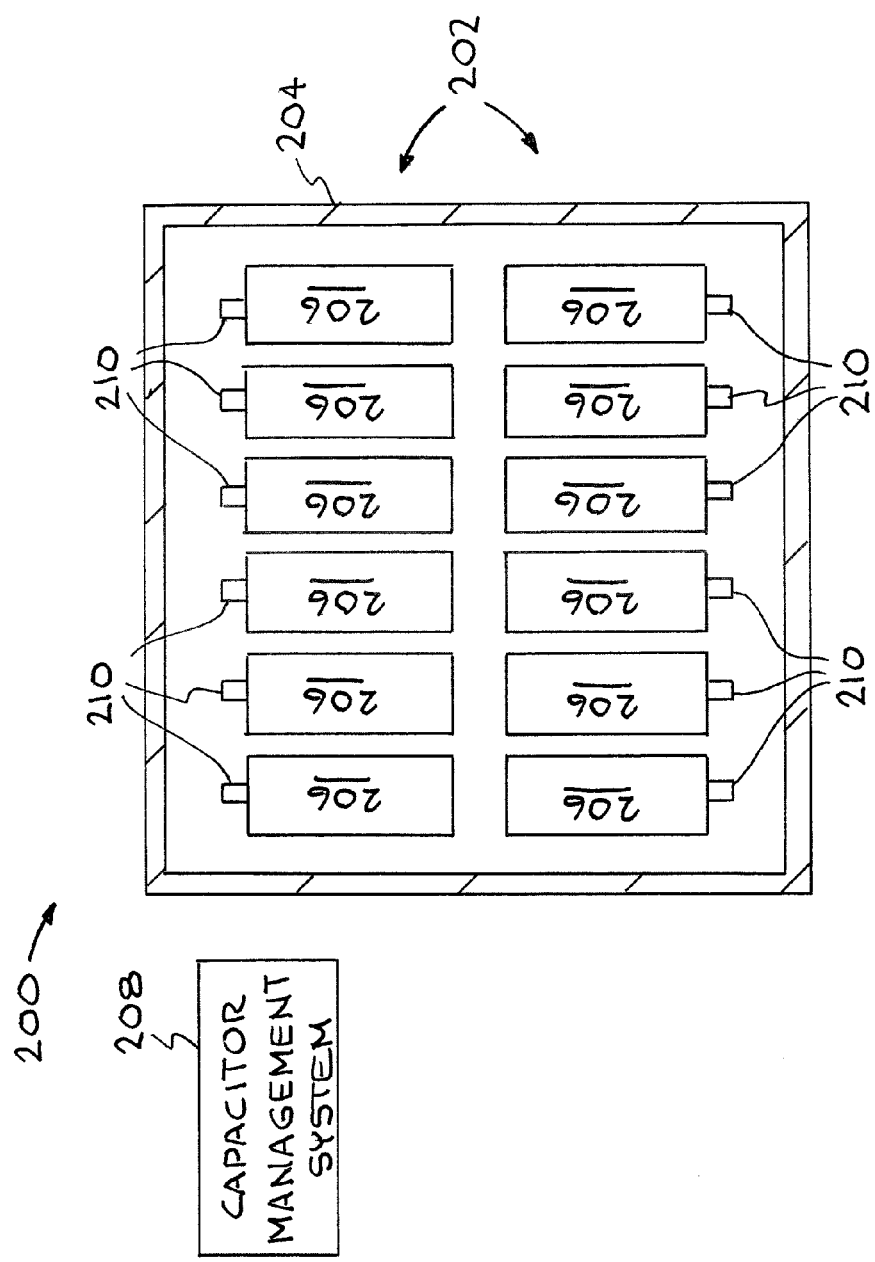
FIG. 2 illustrates a capacitor management system constructed in accordance with the present invention.

Referring now to FIG. 2, an embodiment of a capacitor management system constructed in accordance with the present invention is illustrated. The system is designated generally by the reference numeral 200. The system 200 includes any number of capacitor modules or capacitor packs 202 within a capacitor pack housing 204. Each individual capacitor module or pack 202 includes any number of individual capacitor cells 206. The capacitor module or pack 202 may for example comprise a number of series-connected and/or parallel-connected capacitor cells 202 housed within the capacitor pack housing 204.

Each individual capacitor module or pack 202 includes any number of individual capacitor cells 206 and a corresponding number of Radio Frequency Identification (RFID) sensors 210. A remote capacitor management system 208 is operatively connected to the capacitor module or pack 202, the capacitor cells 206, and the Radio Frequency Identification (RFID) sensors 210 in the housing 204.

The system 200 provides an advanced capacitor management system for the capacitor module or pack 202 and the capacitor cells 206 using the Radio Frequency Identification (RFID) sensors 210. The system 200 enables detection of various events in the capacitor module or pack 202 and the capacitor cells 206. The remote capacitor management system 208 enables remedial action.

Lithium Ion Battery Management System

Figure 3:
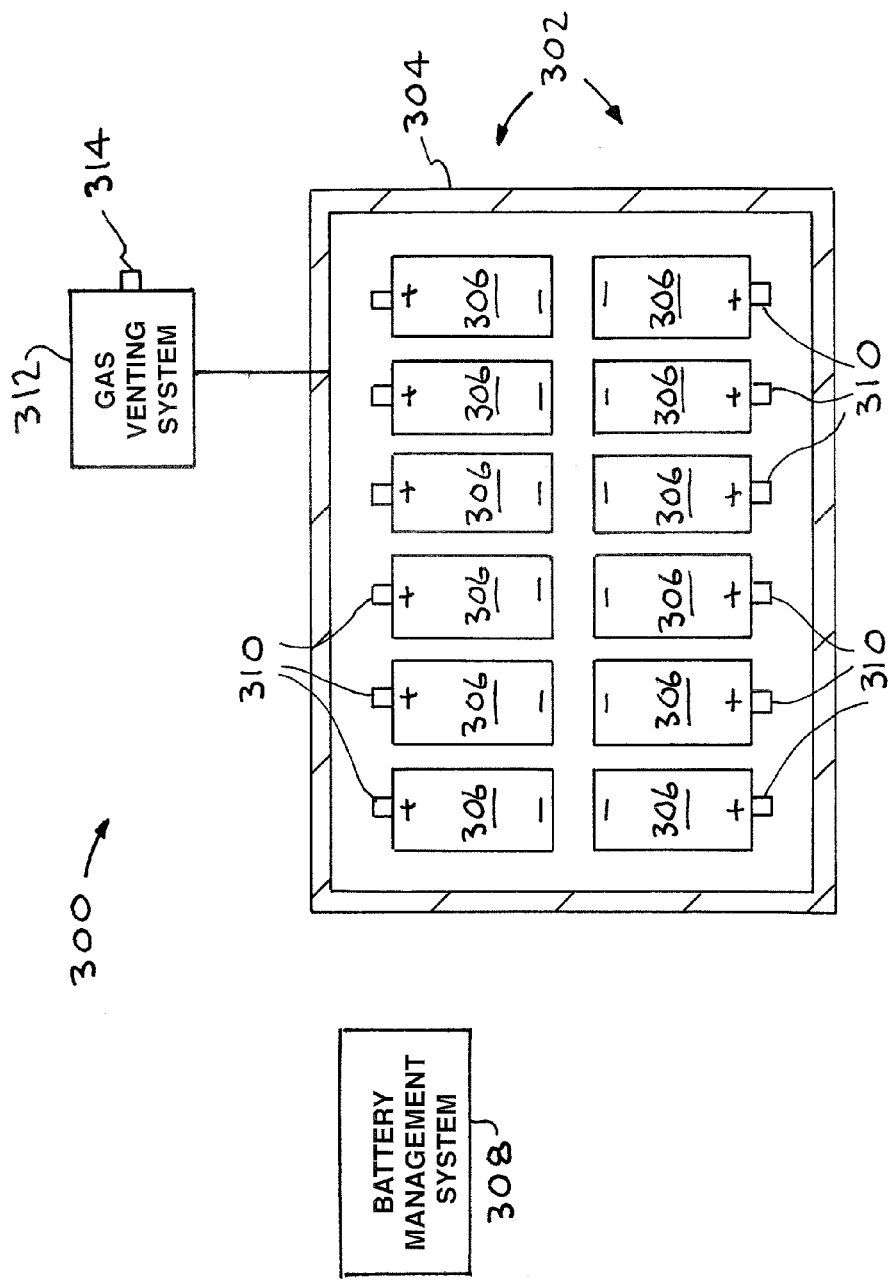
FIG. 3 illustrates a lithium ion battery management system constructed in accordance with the present invention.

Referring now to the drawings and in particular to FIG. 3, an embodiment of a lithium ion battery management system constructed in accordance with the present invention is illustrated. The system is designated generally by the reference numeral 300. The system 300 includes any number of lithium ion battery modules or lithium ion battery packs 302 within a housing 304. Each individual lithium ion battery module or pack 302 includes any number of individual lithium ion battery cells 306. The lithium ion battery module or pack 302 may for example comprise a number of series-connected and/or parallel-connected lithium ion battery cells 302 housed within the lithium ion battery pack housing 304.

Each individual lithium ion battery module or pack 302 includes any number of individual lithium ion battery cells 306 and a corresponding number of Radio Frequency Identification (RFID) sensors 310. A gas venting system 312 is connected to the housing 304. A Radio Frequency Identification (RFID) sensor 314 is connected to the gas venting system 312. A remote lithium ion battery management system 308 is operatively connected to the lithium ion battery module or pack 302, the lithium ion battery cells 306, the Radio Frequency Identification (RFID) sensors 310 in the housing 304, and the Radio Frequency Identification (RFID) sensor 314 connected to the gas venting system 312.

The system 300 provides an advanced lithium ion battery management system for the lithium ion battery module or pack 302 and the lithium ion battery cells 306 using the Radio Frequency Identification (RFID) sensors 310. The system 300 enables detection of various events in the lithium ion battery module or pack 302 and the lithium ion battery cells 306. The remote lithium ion battery management system 308 enables remedial action.

One critical issue facing widespread adoption of rechargeable lithium ion batteries in large scale, is safety. Once these batteries reach internal temperatures of approximately 90° C., self-sustaining exothermic reactions trigger dangerous thermal runaway. The cause of these events can be internal or external short from a variety of causes, included crushing, containment penetration, external heating events, or manufacturing defects. In addition, these batteries are also significantly overdesigned to compensate capacity loss through cycling at moderately high temperatures, with significant capacity loss occurring above ~50° C. for virtually every commercially applicable cell chemistry. Furthermore, these batteries contain a low thermal conductivity plastic (e.g., polyethylene or polypropylene) separator soaked in a non-aqueous electrolytic solution. As a result, when multiple cells are stacked together, it is difficult to remove heat from the more thermally insulated portions of the battery. This makes mitigation of thermal runaway even more difficult, and can cause localized cycling of the battery, which can lead to premature aging. A solution to these problems is provided by Applicant's battery management system 300 that is integral to the battery pack and/or individual cells. When a thermal runaway event is beginning to occur it is sensed by, either active or passive, sensors 310/314. The remote lithium ion battery management system 308 is an advanced battery management system using the Radio Frequency Identification (RFID) sensors 310. The system 300 enables detection of various events in the lithium ion battery module or pack 302 and the lithium ion battery cells 306.

Referring again to FIG. 3, a system is illustrated that in one embodiment can consist of large series-parallel arrays of high performance lithium ion battery cells. The system 300 enables the early detection of various events in the high capacity lithium ion battery packs to provide rapid response to prevent and suppress such events before the results become catastrophic. The distributed wireless sensors 310/314 enable the detection of various parameter including one or more of the following parameters: cell voltage, cell current, cell impedance, cell temperature, cell internal pressure, stress and strain in the cell package, electrolyte leakage, gas evolution and leakage, optical and nuclear particle transmission and scattering, and any pyrotechnic displays internal to the lithium ion battery pack that may be attributed to the onset of thermal runaway. The sensors 310/314 may be either active or passive, with communication possible via the RFID components. Once the sensors 310/314 detect the onset of an event, the signal is used to appropriately manage pack operation (charge and discharge), and remedial action systems will be activated.

The system 300 also leverages specialized computer models and codes as control algorithms in a smart lithium ion battery management system (BMS) unique attributes, enables simultaneous solution of those equations that account for the flow of fluid and heat, chemical reactions, current flow and mechanical stress. The equations that describe electrode kinetics and ionic transport will be integrated into the code. This modeling enables designers to account for subtle, but very important effects such as damage of local circuitry and other vehicular components by the pyrotechnic venting of hot gases. Effective cooling systems, and engineered "fire breaks" and "internal fire suppression methods" can be included. The system 300 has many uses, for example the system 300 has use in connection with high capacity lithium ion lithium ion battery packs for electric and hybrid-electric vehicles, naval systems, aerospace systems, grid storage, and uninterruptable power supplies.

Lithium Ion Battery Management System with Fire Suppression

Figure 4:
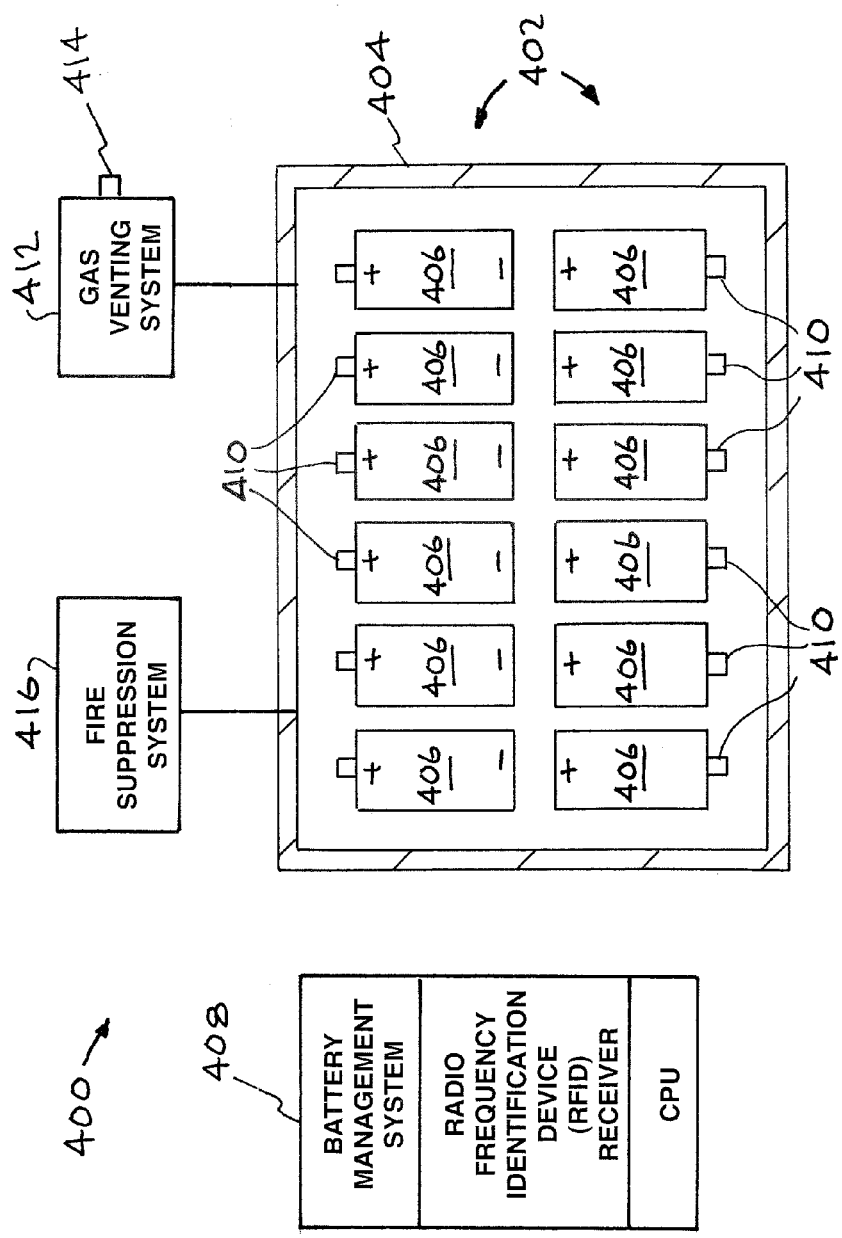
FIG. 4 illustrates a lithium ion battery management system with fire suppression.

Referring now to the drawings and in particular to FIG. 4, an embodiment of a lithium ion battery management system constructed in accordance with the present invention is illustrated. The system is designated generally by the reference numeral 400. The system 400 includes any number of lithium ion battery modules or lithium ion battery packs 402 within a housing 404. Each individual lithium ion battery module or pack 402 includes any number of individual lithium ion battery cells 406. The lithium ion battery module or pack 402 may for example comprise a number of series-connected and/or parallel-connected lithium ion battery cells 402 housed within the lithium ion battery pack housing 404.

Each individual lithium ion battery module or pack 402 includes any number of individual lithium ion battery cells 406 and a corresponding number of Radio Frequency Identification (RFID) sensors 410. A gas venting system 412 is connected to the housing 404. A Radio Frequency Identification (RFID) sensor 414 is connected to the gas venting system 412. A remote lithium ion battery management system 408 is operatively connected to the lithium ion battery module or pack 402, the lithium ion battery cells 406, the Radio Frequency Identification (RFID) sensors 410 in the housing 404, and the Radio Frequency Identification (RFID) sensor 414 connected to the gas venting system 412.

The system 400 provides an advanced lithium ion battery management system for the lithium ion battery module or pack 402 and the lithium ion battery cells 406 using the Radio Frequency Identification (RFID) sensors 410. The system 400 includes a fire suppression system 416 operatively connected to the housing 404 and the lithium ion battery management system 408. The system 400 enables detection of various events in the lithium ion battery module or pack 402 and the lithium ion battery cells 406. The remote lithium ion battery management system 408 enables remedial action using the fire suppression system 416.

Referring again to FIG. 4, a system is illustrated that in one embodiment can consist of large series-parallel arrays of high performance lithium ion battery cells. The system 400 enables the early detection of various events in the high capacity lithium ion battery packs to provide rapid response to prevent and suppress such events before the results become catastrophic. The distributed wireless sensors 410/414 enable the detection of various parameter including one or more of the following parameters: cell voltage, cell current, cell impedance, cell temperature, cell internal pressure, stress and strain in the cell package, electrolyte leakage, gas evolution and leakage, optical and nuclear particle transmission and scattering, and any pyrotechnic displays internal to the lithium ion battery pack that may be attributed to the onset of thermal runaway. The sensors 410/414 may be either active or passive, with communication possible via the RFID components. Once the sensors 410/414 detect the onset of an event, the signal is used to appropriately manage pack operation (charge and discharge), and remedial action systems will be activated. The remote lithium ion battery management system 408 enables remedial action using the fire suppression system 416.

The system 400 also leverages specialized computer models and codes as control algorithms in a smart lithium ion battery management system (BMS) unique attributes, enables simultaneous solution of those equations that account for the flow of fluid and heat, chemical reactions, current flow and mechanical stress. The equations that describe electrode kinetics and ionic transport will be integrated into the code. This modeling enables designers to account for subtle, but very important effects such as damage of local circuitry and other vehicular components by the pyrotechnic venting of hot gases. Effective cooling systems, and engineered "fire breaks" and "internal fire suppression methods" can be included. The system 400 has many uses, for example the system 400 has use in connection with high capacity lithium ion lithium ion battery packs for electric and hybrid-electric vehicles, naval systems, aerospace systems, grid storage, and uninterruptable power supplies.

Figures 5, 6:
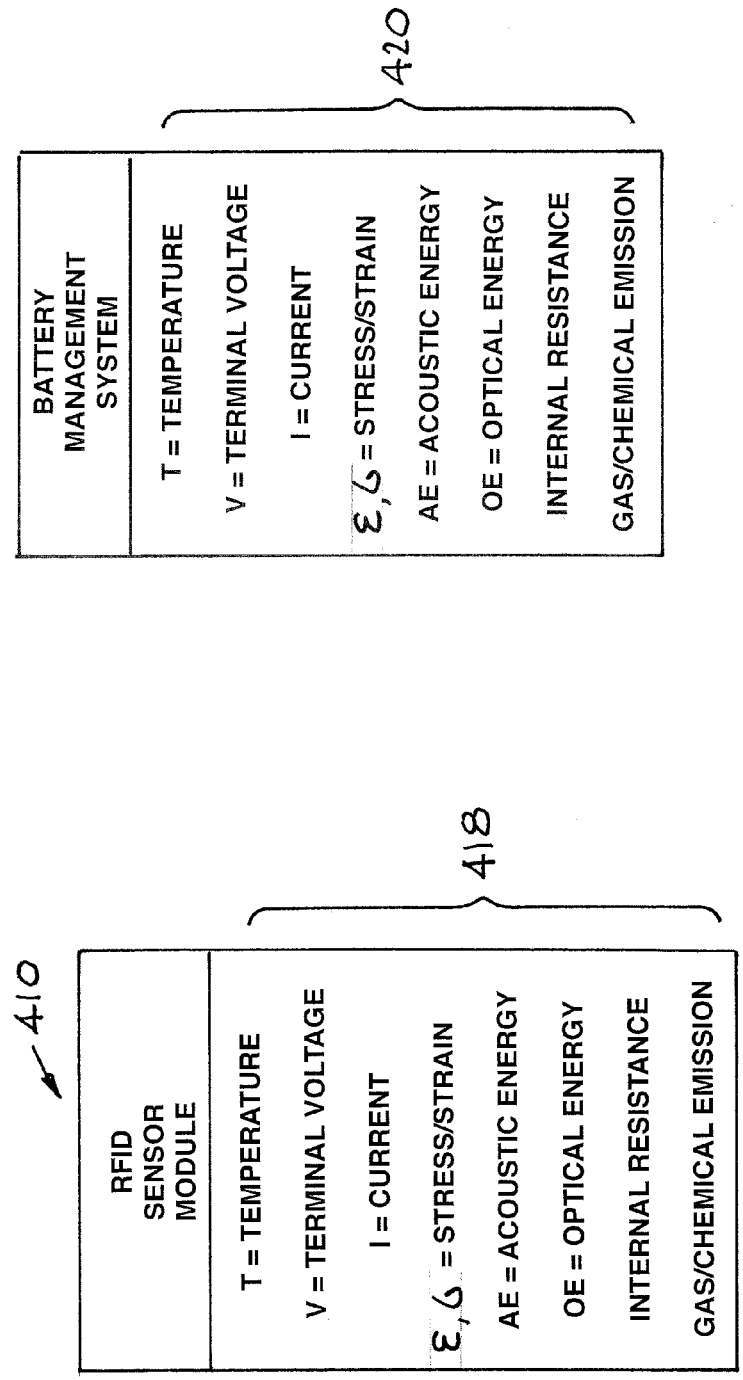
FIG. 5 illustrates additional details of the RFID sensor module of the system illustrated in FIG. 4.
FIG. 6 illustrates additional details of the battery management system illustrated in FIG. 4.

Referring now to FIG. 5, additional details of the RFID sensor module of the system illustrated in FIG. 4 is shown. Each individual lithium ion battery module or pack 402 includes any number of individual lithium ion battery cells 406 and a corresponding number of Radio Frequency Identification (RFID) sensors 410. The distributed wireless sensors 410 enable the detection of various parameters 418 including one or more of the following parameters: cell voltage, cell current, cell impedance, cell temperature, cell internal pressure, stress and strain in the cell package, electrolyte leakage, gas evolution and leakage, optical and nuclear particle transmission and scattering, and any pyrotechnic displays internal to the lithium ion battery pack that may be attributed to the onset of thermal runaway. The sensors 410 may be either active or passive, with communication possible via the RFID components. Once the sensors 410 detect the onset of an event, the signal is used to appropriately manage pack operation (charge and discharge), and remedial action systems will be activated.

Referring now to FIG. 6, additional details of the battery management system illustrated in FIG. 4 are shown. A remote lithium ion battery management system 408 is operatively connected to the lithium ion battery module or pack 402, the lithium ion battery cells 406, the Radio Frequency Identification (RFID) sensors 410 in the housing 404, and the Radio Frequency Identification (RFID) sensor 414 connected to the gas venting system 412. The distributed wireless sensors 410/414 enable the detection of various parameters 420 including one or more of the following parameters: cell voltage, cell current, cell impedance, cell temperature, cell internal pressure, stress and strain in the cell package, electrolyte leakage, gas evolution and leakage, optical and nuclear particle transmission and scattering, and any pyrotechnic displays internal to the lithium ion battery pack that may be attributed to the onset of thermal runaway.

RFID Sensor in Passive Mode

Figure 7:
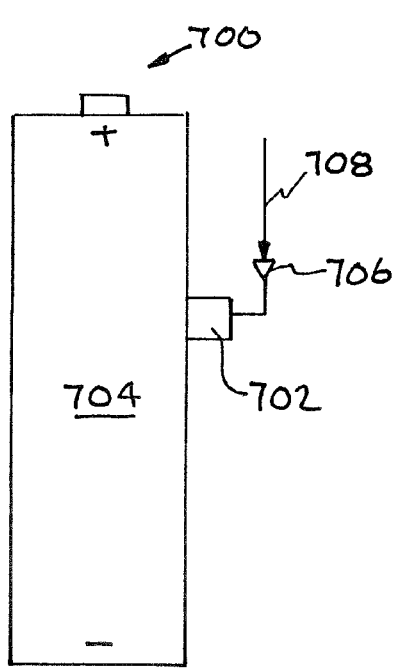
FIG. 7 illustrates an individual RFID tag/sensor in a completely passive mode, obtaining all energy for operation from an antenna.

Referring now to FIG. 7, a radio frequency identification and sensor unit is shown connected to an individual lithium ion battery cell. The radio frequency identification and sensor unit and lithium ion battery cell are designated generally by the reference numeral 700. As shown in FIG. 7, a radio frequency identification and sensor unit 702 is connected to an individual lithium ion battery cell 704. The radio frequency identification and sensor unit 702 includes an antenna 706. Energy, represented by the arrow 708, is transferred to the radio frequency identification and sensor unit 702 through the antenna 706.

The RFID tag/sensor 702 is in a completely passive mode and obtains all energy 708 for operation from the antenna 706. In operation the RFID tag/sensor 702 uses power for radio frequency transmission of the parameters of the individual lithium ion battery cell 704. The transmissions are received by the management system that monitors the parameters of the lithium ion battery pack.

RFID Sensor in Active Mode

Figure 8:
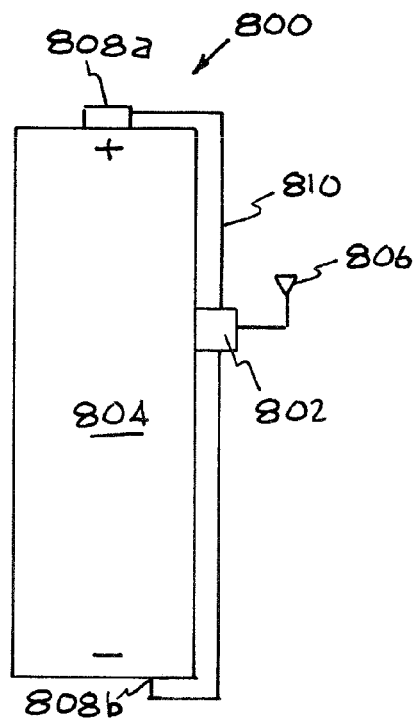
FIG. 8 illustrates an individual RFID tag/sensor in an active mode, obtaining the required energy from operation from the positive and negative terminals of the cell.

Referring now to FIG. 8, another embodiment of a radio frequency identification and sensor unit is shown connected to an individual lithium ion battery cell. The radio frequency identification and sensor unit and lithium ion battery cell are designated generally by the reference numeral 800. As shown in FIG. 8, a radio frequency identification and sensor unit 802 with antenna 806 is connected to an individual lithium ion battery cell 804. The RFID tag/sensor 802 is shown in an active mode, obtaining the required energy for operation from the positive 808a and negative 808b terminals of the cell 804. The lead lines 810 show that the positive 808a and negative 808b terminals of the cell 804 are connected to the lithium ion battery cell 804 to enable the RFID tag/sensor 802 to obtain power for operation from the cell 804.

Tag Circuit with Variable Frequency Electromagnetic Stimulus

Figure 9:
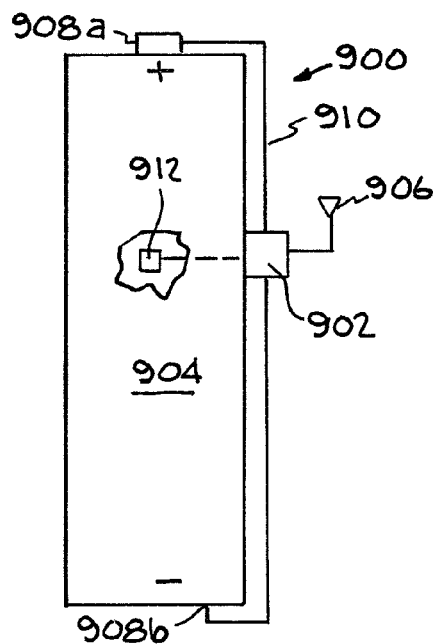
FIG. 9 illustrates a tag circuit that includes the cell with a variable frequency electromagnetic stimulus.

Referring now to FIG. 9, another embodiment of a radio frequency identification and sensor unit is shown connected to an individual lithium ion battery cell. This embodiment is designated generally by the reference numeral 900. As shown in FIG. 9, a radio frequency identification and sensor unit 902 with antenna 906 is connected to an individual lithium ion battery cell 904. The embodiment 900 includes a tag circuit 912 connected to the cell 904. The RFID tag/sensor 902 is shown connected to the positive 908a and negative 908b terminals of the cell 904. The lead lines 910 show that the positive 908a and negative 908b terminals of the cell 904 are connected to the tag circuit 912.

The tag circuit 912 provides a variable frequency electromagnetic stimulus with amplitude and phase. The embodiment 900 monitors the amplitude and phase to sense the internal impedance of the cell 904. The management system monitors the transmissions from the radio frequency identification and sensor unit 902 and monitors the internal impedance of the cell 904. The system provides a variable frequency electromagnetic stimulus that ranges in frequency from 0.001 to 500,000 Hertz and the radio frequency identification and sensor unit 902 monitors the variable frequency electromagnetic stimulus that ranges in frequency from 0.001 to 500,000 Hertz to sense the internal impedance of the cell 904.

Figure 10:
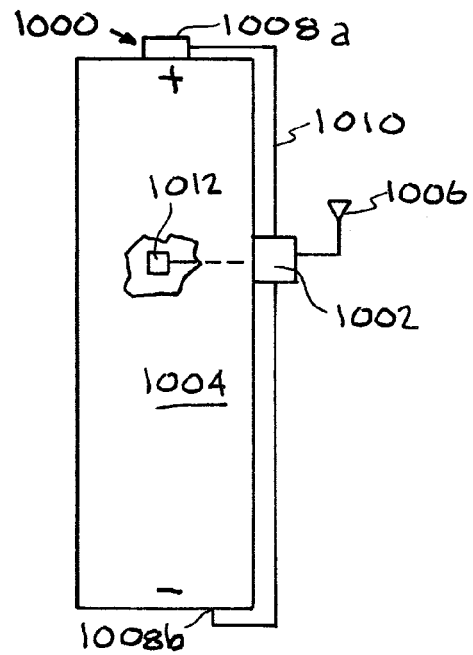
FIG. 10 illustrates the embedding of temperature sensors into the cell, to directly measure the core temperature.

Referring now to FIG. 10, the embedding of a temperature sensor into the cell to directly measure the core temperature of the cell is shown. The Embedded temperature sensor system is designated generally by the reference numeral 1000. As shown in FIG. 10, a radio frequency identification and sensor unit 1002 with antenna 1006 is connected to an individual lithium ion battery cell 1004. The RFID tag/sensor 1002 is shown connected to the positive 1008a and negative 1008b terminals of the cell 1004. The lead lines 1010 show that the positive 1008a and negative 1008b terminals of the cell 1004 are connected to the RFID tag/sensor 1002. An embedded temperature sensor 1012 is located in the core of the lithium ion battery cell 1004 and directly measures the core temperature of the cell 1004. The management system monitors the transmissions from the radio frequency identification and sensor unit 1002 and monitors the core temperature of the lithium ion battery cell 1104.

Monitoring Acoustic Emissions—Early Indicators of Failure

Figure 11:
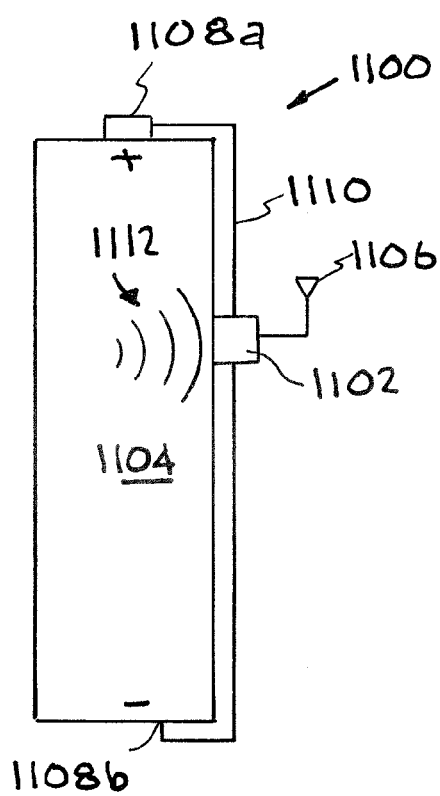
FIG. 11 illustrates monitoring acoustic emissions wirelessly as early indicators of failure in electrochemical cells, and high energy density capacitors.

Referring now to FIG. 11, the monitoring acoustic emissions wirelessly as early indicators of failure in electrochemical cells, and high energy density capacitors is illustrated. The monitoring acoustic emissions system is designated generally by the reference numeral 1100.

As shown in FIG. 11, a radio frequency identification and sensor unit 1102 with antenna 1106 is connected to an individual lithium ion battery cell 1104. The RFID tag/sensor 1102 is shown connected to the positive 1108a and negative 1108b terminals of the cell 1104. The lead lines 1110 show that the positive 1108a and negative 1108b terminals of the cell 1104 are connected to the RFID tag/sensor 1102.

The system 1100 for monitoring parameters of a lithium ion battery cell 1104 includes monitoring acoustic emissions 1112 as early indicators of failure of the cell 1104. The radio frequency identification and sensor unit 1102 senses the acoustic emissions 1112 and monitors the acoustic emissions as early indicators of failure of the cell 1102.

Monitoring Optical Emissions—State-of-Health of Cell

Figure 12:
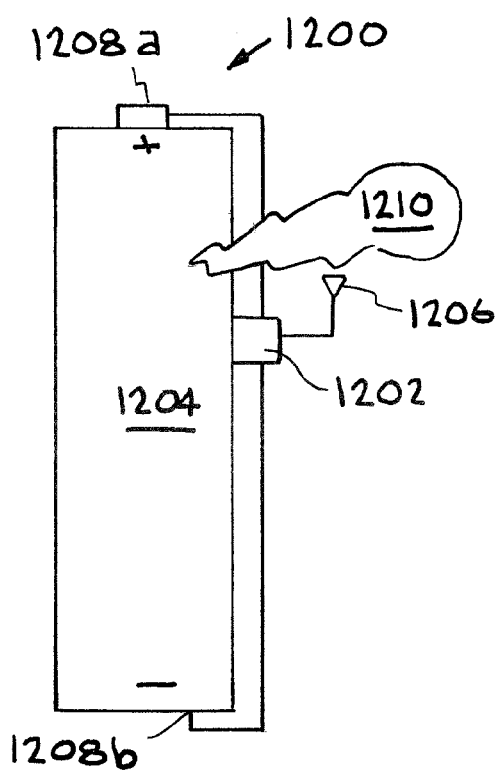
FIG. 12 illustrates monitoring pyrotechnic displays internal to the battery pack that may be attributed to the onset of thermal runaway.

Referring now to FIG. 12, the monitoring optical emissions due to the pyrotechnic displays that accompany venting and early indications of the state-of-health of the cell is illustrated. The monitoring of optical emissions system is designated generally by the reference numeral 1200.

As shown in FIG. 12, a radio frequency identification and sensor unit 1202 with antenna 1206 is connected to an individual lithium ion battery cell 1204. The RFID tag/sensor 1202 is shown connected to the positive 1208a and negative 1208b terminals of the cell 1204. The system 900 for monitoring optical emissions due to the pyrotechnic displays that accompany venting and early indications of the state-of-health of the cell of a lithium ion battery cell 1204 includes monitoring acoustic emissions 1210. The radio frequency identification and sensor unit 1202 senses the optical emissions 1210 due to the pyrotechnic displays that accompany venting and early indications of the state-of-health of the cell of the cell 1202.

Additional Background Information

Power transmission networks sometimes utilize backup power systems to compensate for varying power generation and load, and in extreme cases the complete loss of power. Our increasing reliance on renewable sources of energy such as wind, wave and solar will make our ability to operate with fluctuating sources even more important. High capacity battery backup systems will provide power during fluctuations of the generated wind or solar power and even during power outages.

Such backup power systems rely on large banks of batteries configured in series-parallel arrays to store enough energy to provide a steady flow of electricity, even in the face of wildly varying fluctuations from renewable sources. In power transmission networks such battery storage systems will consist of a very large number of individual electrochemical cells, such as lithium ion cells, connected in series and parallel to enable the overall system to achieve required levels of voltage and current. Ultimately, such systems may be required to provide current to electrical buses that operate at tens to thousands of volts, and may be required to deliver power levels ranging from hundreds of watts to millions of watts. To achieve this, such battery energy storage systems will comprise several thousands battery cells.

Batteries required for backup power applications are required to store very large amounts of energy. Any individual cell in such a system experiencing c either an external or internal short circuit, over charging, or over discharging, will quickly become very hot. In the case of lithium ion cells, the chemistry is such that the cell will enter a regime known as thermal runaway at relatively modest threshold temperatures (perhaps as low as 60° C.). The heat generated by a failing cell during thermal runaway flow out of the cell, thereby heating adjacent cells, with catastrophic cell-to-cell propagation. The heat generated by the highly exothermic reactions will heat one cell after the other, thereby causing a huge fire. This scenario poses one of the most severe hazards in the modern energy storage field, and has caused the catastrophic failure of terrestrial, naval, and aerospace vehicles.

An added complication in the case of large series-parallel arrays of lithium-ion cells is the need for individual cell balancing during charging, to prevent any single sell in the system from being inadvertently overcharged. In essence, the battery management system, and associated array of voltage sensors and current control electronics, must assure that no individual cell can exceed a maximum charge voltage during charging of the entire system. In the case of lithium-ion systems, this maximum terminal voltage is typically 4.2 volts for batteries constructed with lithium-cobalt oxide cathode materials.

During thermal runaway, cells can violently vent, releasing hot burning gases capable of burning through thick sheets of steel and other alloys. In the case of a lithium-ion cell, gases released during venting may contain a complicated mixture, including hydrogen, hydrogen fluoride, carbon monoxide, carbon dioxide, methane, ethane, methylene, propylene, organic carbonates and also carbon powder.

During the past fifteen years, lithium-ion batteries have replaced the nickel-cadmium and nickel-metal hydride batteries in our cell phones, laptop computers, digital cameras, radios and personal entertainment devices, have replaced silver-zinc batteries in underwater vehicles important to national security, are used aboard strategic military aircraft and satellites, have found their way to Mars, and traveled over the Martian surface aboard roving robots, and are in the process of replacing other battery technology in terrestrial vehicles and robotics. Virtually all of the Federal Governments emphasis on advanced battery technology for hybrid electric and plug-in electric vehicles centers around the design and development of high-performance lithium ion battery packs, with the future of our domestic auto industry hanging on the fate of the battery industry in the United States. Unfortunately, much of this technology, including that needed for national security is now designed and manufactured abroad. Despite decades of conventional safety testing serious problems remain. Lithium-ion explosions and fires occur frequently in both products and manufacturing plants.

Despite the proliferation of this technology, numerous catastrophic events have now occurred, with batteries the size of those used in our cell phones, to multi-megawatt batteries used for national defense. Problems have been encountered with lithium ion batteries aboard aircraft. For example:

Aug. 8, 2008, Washington, D.C. to Dallas: a passenger noticed the lithium ion battery in his laptop computer was smoking.

Mar. 18, 2008, Denver, Colo.: A united airlines employee burned his hand when lithium ion batteries in a flashlight exploded in the jet's cockpit on the ground.

Mar. 4, 2008, Chicago, Ill. to Tokyo, Japan: A video player emitted a 10-inch shower of sparks whit in the lithium-ion battery ignited on a United flight.

The Pilots Union has lobbied to ban lithium and lithium ion batteries from flights due to fires that have occurred with devices brought onboard planes by passengers. In shipping tests intended to simulate the pressurization cycles experienced in air transport, the polymer gels have experience swelling, seal failure and leakage problems. The electrolyte is held in in thermally laminated seams.

The modern lithium-ion battery has: an anode that consists of a graphite-based active material (Li—C6) with carbon filler and PVDF binder coated onto a copper foil current collector; a cathode that consists of a transition metal oxide or iron phosphate (Li—NiO2, Li—CoO2, Li—MnO2, or Li—FePO4) active material with a PVDF binder coated onto an aluminum foil current collector; a microporous porous polyethylene separator, and an electrolyte consisting of a mixed organic carbonate solvent (EC:DMC:DEC) and LiPF6 sal. The liquid cylindrical or prismatic cells are contained in a hermetically sealed metal can, while polymer-gel cells are contained in a soft aluminum-polyethylene laminate package, with thermally laminated seams. In the case of the polymer-gel cell, the polyethylene separator is usually coated on both sides with porous PVDF layers. This battery should probably be able to operate from −40 to +60° C. The open-circuit voltage is 4.2 V, with operation between 4.2 and 3.0 V (possibly as low as 2.8 V). The specific power, power density, specific energy and energy density are 1100-74 W/kg, 2270-147 W/L, 75-182 Wh/kg, and 139-359 Wh/L, respectively.

Figure 13:
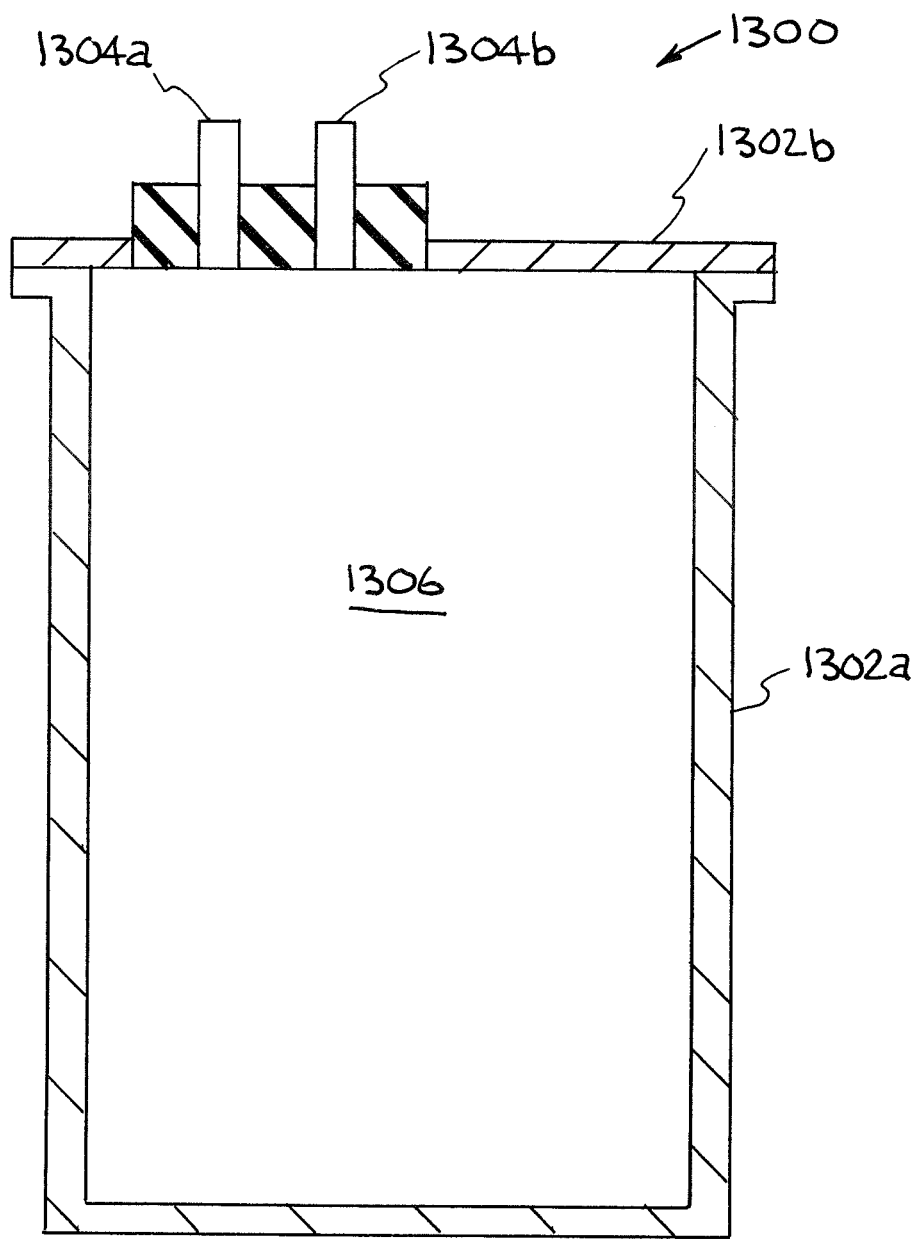
FIG. 13 illustrates a high performance Li-Ion cell.

Referring now to FIG. 13, a high performance Li-Ion cell is illustrated. The high performance Li-Ion cell is designated generally by the reference numeral 1300. The cell 1300 is a commercial 3-Ah polymer gel cell. The cell 1300 has a lower housing 1302*a* and an upper housing 1302*b*. Terminals 1304*a* and 1304*b* project from the upper housing 1302*b*. The upper housing 1302*b* and lower housing 1302*a* contain the active material (Li—C6) and the other components of the cell 1300.

Figure 14:
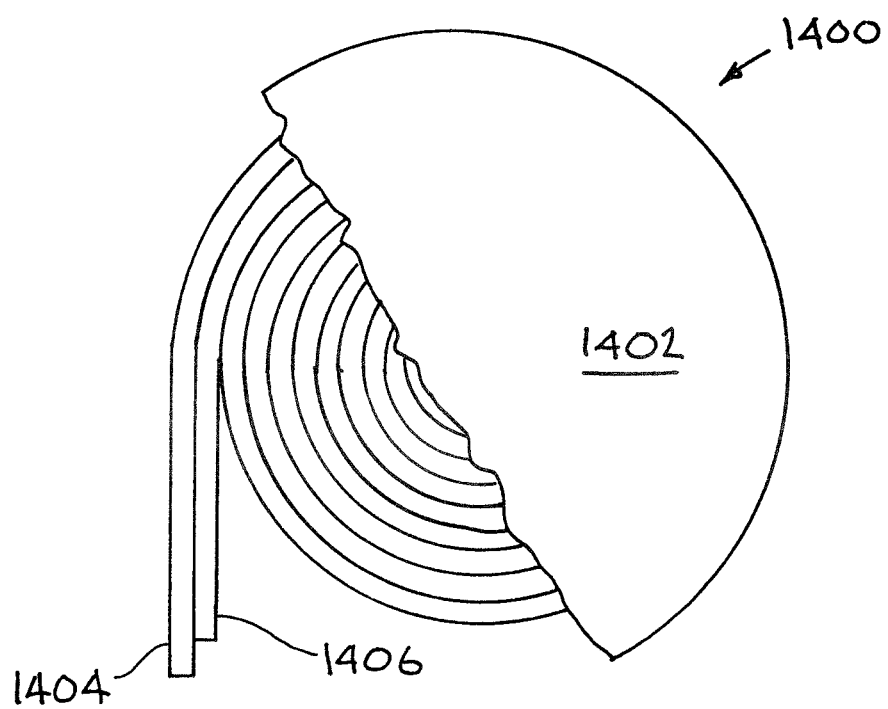
FIG. 14 illustrates a high quality jelly roll for a polymer gel cell.

Referring now to FIG. 14, a high quality jelly roll for a polymer gel cell is illustrated. The high quality jelly roll is designated generally by the reference numeral 1400. A housing 1402 contains the high quality jelly roll 1400 and provides a high performance Li-Ion cell. The high quality jelly roll 1400 is produced by an automatic winder. The high quality jelly roll 1400 includes a 20-micron PVDF-coated microporous polyethylene separator 1404, a $Li_xCoO_2$ cathode material with PVDF binder coated onto a 15 to 25 micron thick Al foil 1406, and a $Li_xC_6$ anode material with PVDF binder coated onto 15 to 25 micron thick Cu foil (not visible).

The cycle life of the best state-of-the-art lithium-ion batteries can be as great as 1500 cycles (to 80% of the original capacity). However, poorly constructed cells can have much shorter lives (300 cycles representing poorer cells). Based upon published data, the cost of energy storage is believed to be approximately $300 per kilowatt-hour (though some quote $1000 per kilowatt-hour).

Figure 15:
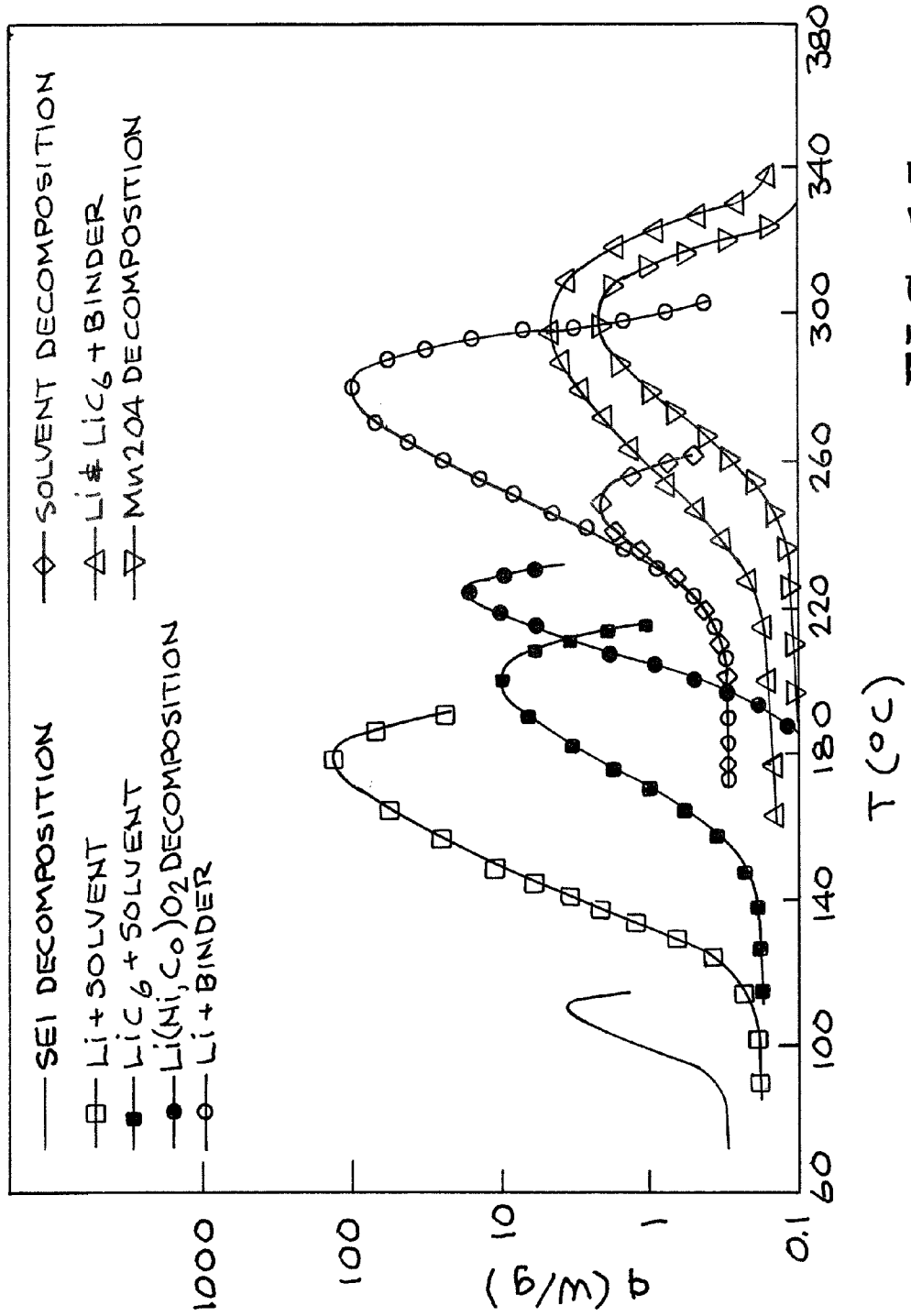
FIG. 15 illustrates the sequence of chemical reactions encountered in Li-ion cell during runaway.

As a lithium ion battery begins to undergo heating, which can be caused by ohmic heating, internal shorting, or the application of heat from outside the cell, a sequence of chemical reactions occur within the Li-ion system, ultimately leading to thermal runaway. The types of chemical reactions that occur, and that must be accounted for in the proposed code development are illustrated in FIG. 15. Ideally, the inside of the Li-ion cell is oxygen-free, enough oxygen can be liberated from the disproportionation of the transition metal oxide active material in the cathode to support limited combustion of the organic carbonate solvents in the electrolyte. Relevant reactions are illustrated in FIG. 16.

Figure 17:
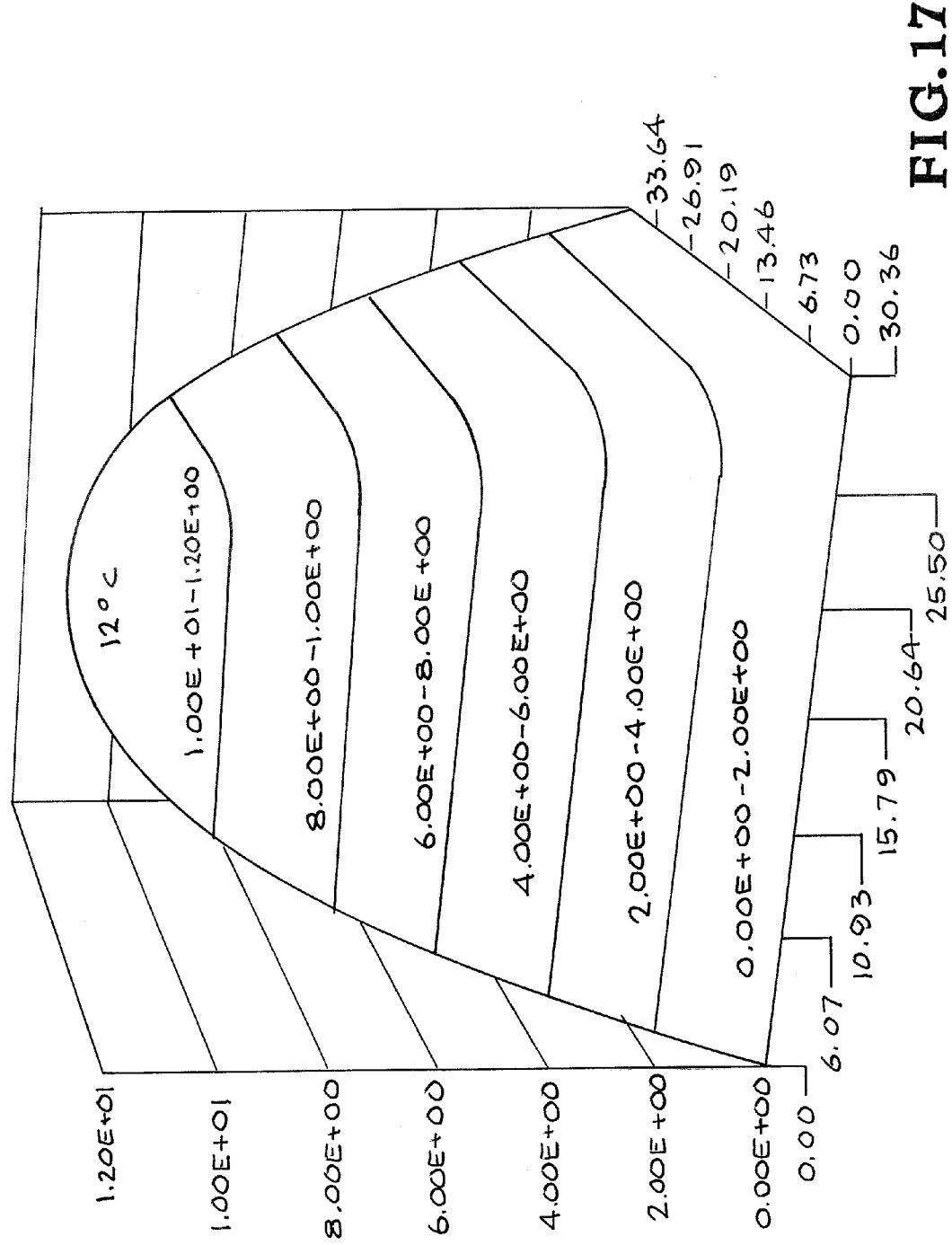
FIG. 17 illustrates simulations of temperature profiles developing in lithium-ion battery during normal charging conditions, which show a modest steady-state core-temperature of about 12° C., which insufficient to drive the system into thermal runaway.
Figure 18:
FIG. 18 illustrates the localized heating effect of an internal short near a corner of the cell, with the onset of thermal runaway in close proximity to the short.

Referring now to FIG. 17, simulations of temperature profiles developing in lithium-ion battery during normal charging conditions are illustrated. FIG. 17 shows a modest steady-state core-temperature of about 12° C., which insufficient to drive the system into thermal runaway. Off normal conditions are more threatening. A second simulation is shown in FIG. 18, illustrating the localized heating effect of an internal short near a corner of the cell, with the onset of thermal runaway in close proximity to the short. Localized internal shorts quickly drive such high performance energy storage systems into thermal runaway, with subsequent propagation to other lithium-ion cells in the battery pack, with further propagation to other packs within the system if they exist. These figures show the importance of placing temperature sensors inside, and on the surface of individual cells, with a high-degree of spatial fidelity. Ideally, one would like to be able to follow the cells core temperature during charge and discharge, which would require incorporation of the temperature sensor inside the cell. This sensor would then communicate via wires to an RFID tag external to the cell, which would wirelessly transmit the temperature measurement to the BMS.

In regard to thermal stability modeling, and to support other accident investigations, the inventors have modeled the effects of internal shorts on localized thermal runaway events using custom codes. The physics of interest are strongly coupled and include:
  Battery chemistry of nominal charge/discharge
  Abnormal ageing at a defect (local chemistry, heat, voltage, stress)
  Electric fields and current flow within the cell
  Heat generation and cell cooling, thermal run-away
  Convection fluid flow within the electrolyte
  External coolant flow
  Stress and material failure due to volumetric changes during charge/discharge cycle
  Chemical deflagration of run-away battery
  Dynamic structural failure of run-away battery cell and battery system The general equation for mass transport in electrochemical systems expresses the flux as the sum of three terms: the first representing diffusion; the second representing electromigration, and the third representing convective transport, due to the presence of flow:

$$J_j = -D_j \nabla C_j - \frac{z_j F}{RT} D_j C_j \nabla \phi + C_j v \quad \text{[Equation 1]}$$

where $J_j$ is the flux of component j, $D_j$ is the diffusivity of component j, $C_j$ is the concentration of component j, $z_j$ is the charge on component j, F is the Faraday's constant, R is the gas constant, T is the absolute temperature, $\phi$ is the electric potential, and v represents the flow field. For linear conduction, this becomes the Nernst-Planck equation:

$$J_j(x) = -D_j \frac{\partial C_j(x)}{\partial x} - \frac{z_j F}{RT} D_j C_j \frac{\partial \phi(x)}{\partial x} + C_j v(x) \quad \text{[Equation 2]}$$

As can be seen in these equations, the application of an electric field enhances the flux of ions, accelerating their movement over that possible in the absence of the electric field. The transient case for an incompressible electrolyte ($\nabla \cdot v = 0$) can be formulated in such a way as to eliminate the flux, and enable the spatially-dependent concentration to be calculated as a function of time:

$$\frac{\partial C_j}{\partial t} + v \cdot \nabla C_j = z_j F \nabla \cdot (u_j C_j \nabla \phi) + \nabla \cdot (D_j \nabla C_j) + R_j \quad \text{[Equation 3]}$$

where $R_j$ represents a homogeneous reaction rate for component$_j$. The potential distribution, which is required to calculate the electromigration term, is obtained from a solution of Poisson's equation, which relates the charge density to the Laplacian of the electric potential:

$$\nabla^2 \phi = -\frac{F}{\varepsilon} \sum_j z_j C_j \quad \text{[Equation 4]}$$

In this equation, $\varepsilon$ is the permittivity or dielectric constant. These equations will have to be included into ALE3D.

Cell impedance is also very important. Electrochemical impedance spectroscopy (EIS) will be used to detect any unexpected change in the impedance of individual lithium ion cells due to potential, temperature or pressure cycling, as well as changes due to mechanical shock and vibration. During EIS, a small amplitude potential modulation (±5 mV) with a variable frequency ranging from 1 mHz to 500 kHz, is applied to the device, around the constant voltage of operation or at the open circuit voltage (OCV). The current response is measured, and impedance spectra constructed. With this wide range of frequencies, it is possible to separate the effects of phenomena inside the electrochemical device with vastly different time and length scales. For example, the double layer capacitance ($10^{-7}$ centimeters, $10^9$ volts per centimeter) can be separated from the electrolyte conductance ($10^{-1}$ centimeters, $10^1$ volts per centimeter), virtually in real time. Despite the power and wide use of this technique, and the opportunity of incorporating this technique as a real-time monitoring strategy in real battery systems, virtually all data is interpreted in terms of crude equivalent circuit models (linear networks of resistors, capacitors, and inductors).

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A system for monitoring parameters of a lithium ion battery pack, wherein the lithium ion battery pack includes a multiplicity of individual lithium ion battery cells, comprising:
- a radio frequency identification and sensor unit connected to each of the lithium ion battery cells that senses the parameter of each individual lithium ion battery cell and provides radio frequency transmission of the parameters of each individual lithium ion battery cell,
- wherein the parameters include internal impedance of the cell;
- wherein said radio frequency identification and sensor unit includes a tag circuit that provides a variable frequency electromagnetic stimulus with amplitude and phase and monitors said amplitude and phase to sense said internal impedance of the cell, and
- a management system that monitors said transmissions from said radio frequency identification and sensor units and monitors the parameters of the lithium ion battery pack,
- wherein said management system that monitors said transmissions from said radio frequency identification and sensor units monitors said internal impedance of the cells of the lithium ion battery pack.

2. The system for monitoring parameters of a lithium ion battery pack of claim 1, wherein said tag circuit that provides a variable frequency electromagnetic stimulus that ranges in frequency from 0.001 to 500,000 Hertz and wherein said radio frequency identification and sensor unit monitors said variable frequency electromagnetic stimulus that ranges in frequency from 0.001 to 500,000 Hertz to sense said internal impedance of the cell.

3. A method of monitoring parameters of a lithium battery pack that includes a multiplicity of individual lithium battery cells, comprising the steps of:
- providing radio frequency identification and detection of each of the individual lithium battery cells for identification and detection of the parameters of each individual lithium battery cell,
- wherein the parameters include internal impedance of the cell,
- wherein said step of providing radio frequency identification and detection of each of the individual lithium battery cells comprises
- providing a tag circuit to produce a variable frequency electromagnetic stimulus with amplitude and phase, and
- monitoring said amplitude and phase to sense said internal impedance of the cell, and
- monitoring said radio frequency identification and detection of each individual lithium battery cell for monitoring the parameters of the lithium battery pack.

* * * * *